(12) United States Patent
Albano

(10) Patent No.: US 8,651,108 B2
(45) Date of Patent: Feb. 18, 2014

(54) INFANT PACIFIER FOR OXYGEN DELIVERY

(76) Inventor: Brian M. Albano, Sevierville, TN (US)

( * ) Notice: Subject to any disclaimer, the term of this patent is extended or adjusted under 35 U.S.C. 154(b) by 97 days.

(21) Appl. No.: 13/385,549

(22) Filed: Feb. 24, 2012

(65) Prior Publication Data

US 2012/0247469 A1    Oct. 4, 2012

Related U.S. Application Data

(60) Provisional application No. 61/516,313, filed on Apr. 1, 2011.

(51) Int. Cl.
*A61J 17/00* (2006.01)
*A62B 7/00* (2006.01)

(52) U.S. Cl.
USPC ............ 128/207.18; 128/200.24; 128/202.16; 606/234

(58) Field of Classification Search
USPC ............. 128/201.18, 204.18, 205.25, 206.21, 128/207.18; 606/234–236
See application file for complete search history.

(56) References Cited

U.S. PATENT DOCUMENTS

| | | | |
|---|---|---|---|
| 4,520,809 A * | 6/1985 | de Greef et al. ......... | 128/200.24 |
| 5,375,593 A | 12/1994 | Press | |
| 5,904,140 A * | 5/1999 | McGoogan .............. | 128/200.24 |
| 7,134,432 B2 * | 11/2006 | Olsen ........................ | 128/200.26 |
| 7,318,433 B2 * | 1/2008 | Cockerham .............. | 128/201.26 |
| 2004/0040556 A1 * | 3/2004 | Fillyaw .................... | 128/202.16 |
| 2010/0000525 A1 * | 1/2010 | Lee et al. ................. | 128/202.13 |
| 2010/0147298 A1 * | 6/2010 | Loescher et al. ......... | 128/203.22 |

FOREIGN PATENT DOCUMENTS

WO    WO 2006125610 A1 * 11/2006

* cited by examiner

*Primary Examiner* — Justine Yu
*Assistant Examiner* — Timothy Stanis
(74) *Attorney, Agent, or Firm* — Luedeka Neely Group, P.C.; Stephen D. Adams

(57) ABSTRACT

An oxygen delivery apparatus for delivery of oxygen to an infant from a source includes a mouthpiece having a body portion and lip-engaging flange portions which surround the body portion and a nipple which extends to one side of the central body portion for acceptance by the mouth of an infant. The body portion of the mouthpiece includes a pair of internal passageways each having an inlet and an outlet and wherein the inlets of the passageways are adapted to accept oxygen delivered thereto from a source and wherein the outlets of the passageways are disposed at locations along the surface of the mouthpiece so that when the nipple is accepted by the mouth of an infant, the outlets of the passageways are disposed adjacent, but not within, the nostrils of the infant.

17 Claims, 2 Drawing Sheets

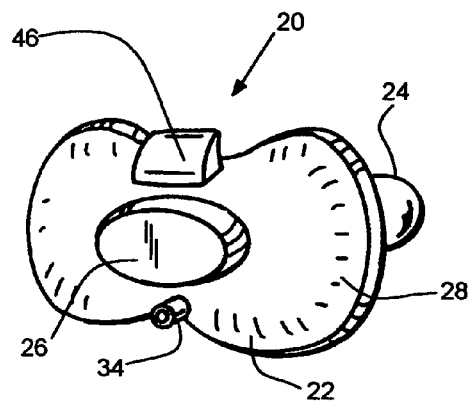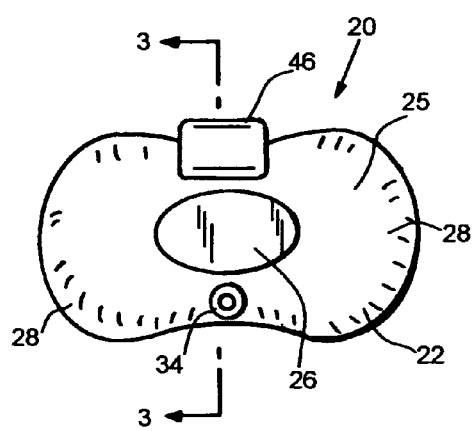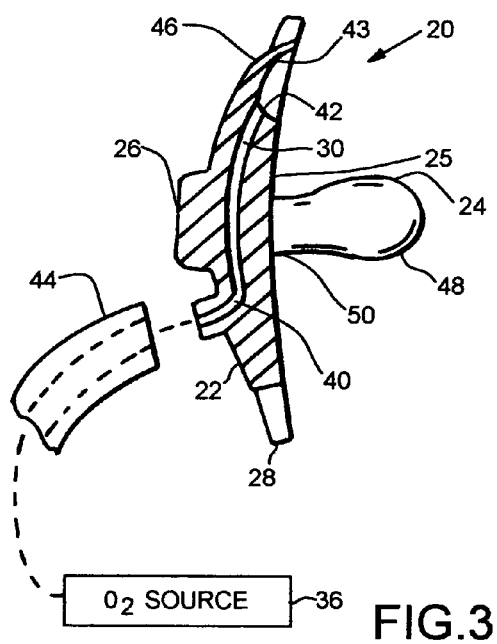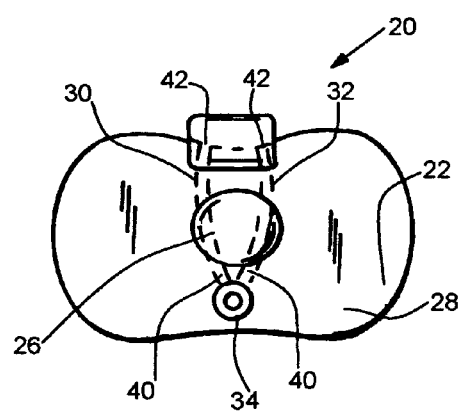
FIG.1
FIG.2
FIG.3
FIG.4

INFANT PACIFIER FOR OXYGEN DELIVERY

The benefit of Provisional Application Ser. No. 61/516,313, filed Apr. 1, 2011 and entitled ALBAN-O$_2$ INFANT PACIFIER FOR OXYGEN DELIVERY is hereby claimed. The disclosure of this referenced provisional patent application is incorporated herein by reference.

BACKGROUND OF THE INVENTION

This invention relates generally to means and methods for delivery of oxygen to a patient and relates, more particularly, to means and methods for delivery of oxygen to the nostrils of a patient who is an infant.

Heretofore, the most common manner for delivering oxygen from a source to the nostrils of an infant was to use a small nasal cannula designed for this purpose. For example, the nasal cannula would likely possess a conduit through which oxygen is conducted from a source and the conduit would, in turn, possess two tubular portions which are supportable across the face of an infant and two nostril orifices disposed between the tubular portions. Typically and to accommodate the use of the nasal cannula by an infant, the two tubular portions are sized (in length) so as to be capable of being draped across the ears of the infant for supporting the nostril orifices in registry with the infant's nostrils for discharge of oxygen from the cannula toward the nostrils. If necessary, the tubular portion of the cannula is commonly taped across the face of the infant to maintain the nostril orifices at desired locations thereon.

Because of the presence of a nasal cannula across the face of an infant is normally foreign to the infant, the infant is likely to resist the nasal cannula—whether it is draped across the infant's ears or whether it is taped to the infant's face.

To render an oxygen delivery cannula less onerous to an infant, the cannula can be incorporated within a pacifier. One attempt to incorporate such a cannula to an infant pacifier is described in U.S. Pat. No. 5,375,593 wherein a pair of nasal cannula are mounted within a mouthpiece of the pacifier for directing air into the nostrils of an infant when the pacifier (or, more specifically, the nipple thereof) is held within the mouth of the infant. However, the pacifier of this referenced patent does not resemble a pacifier that the infant is likely to be familiar with nor does it address the potential discomfort experienced by the infant from the presence of the nasal cannula within the infant's nostrils.

It would be desirable to provide an alternative means for delivering oxygen to the nostrils of an infant wherein the alternative means resembles a pacifier which the infant is likely to be familiar with and is adapted to direct oxygen toward the nostrils of the infant without the insertion of nasal cannula within the nostrils.

Accordingly, it is an object of the present invention to provide a new and improved oxygen delivery apparatus for an infant which is intended to promote the infant's comfort when oxygen is delivered toward the infant's nostrils.

Another object of the present invention is to provide such an oxygen delivery apparatus which embodies features of a commonly-used pacifier with which an infant is likely to be familiar.

Still another object of the present invention is to provide such an oxygen delivery apparatus which obviates the need for the insertion of nasal cannula directly within the nostrils of an infant.

Yet another object of the present invention is to provide such an oxygen delivery system which is uncomplicated in structure, yet effective in operation.

SUMMARY OF THE INVENTION

This invention resides in an oxygen delivery apparatus for delivery of oxygen to an infant from a source.

The apparatus includes a mouthpiece having a body portion and lip-engaging flange portions which surround the body portion, and the apparatus further includes a nipple which extends from the body portion for acceptance by the mouth of an infant. In addition, the body portion of the mouthpiece includes a pair of internal passageways each having an inlet and an outlet and wherein the inlets of the passageways are adapted to accept oxygen delivered thereto from a source and wherein the outlets of the passageways are disposed at locations along the surface of the mouthpiece so that when the nipple is accepted by the mouth of an infant, the outlets of the passageways are disposed adjacent, but not within, the nostrils of the infant.

BRIEF DESCRIPTION OF THE DRAWINGS

FIG. 1 is a perspective view of a oxygen-delivery apparatus within which features of the present invention are embodied.

FIG. 2 is a front elevation view of the FIG. 1 apparatus as seen generally from the left in FIG. 1.

FIG. 3 is a cross-sectional view taken about on line 3-3 of FIG. 2.

FIG. 4 is a front elevational view similar to that of FIG. 2 but illustrating the paths traced by the oxygen-conducting passageways through the interior of the mouthpiece of the apparatus.

DETAILED DESCRIPTION OF THE ILLUSTRATIVE EMBODIMENTS

Figure 5:
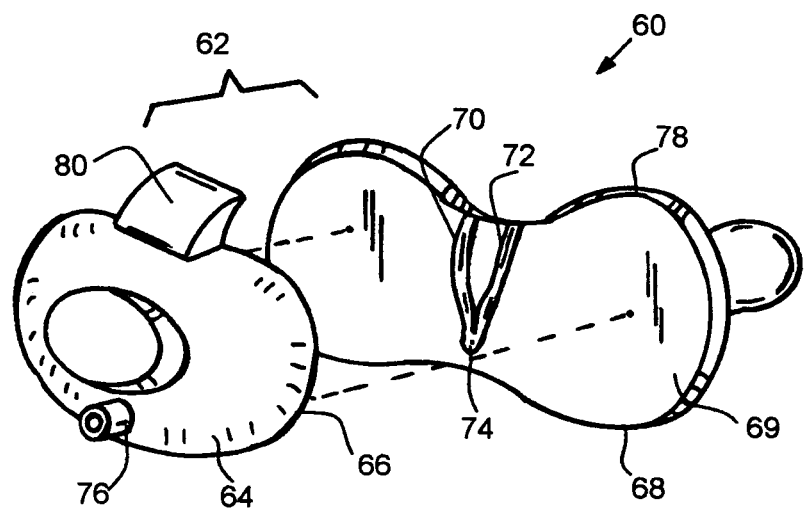
FIG. 5 is a perspective view of an alternative oxygen-delivery apparatus, shown exploded, within which features of the present invention are embodied.

Turning now to the drawings in greater detail and considering first FIGS. 1-4, there is illustrated an embodiment, generally indicated 20, of an oxygen-delivery apparatus within which features of the present invention are embodied. The apparatus 20 is in the form of a pacifier adapted to be held in the mouth of an infant and, to this end, includes a mouthpiece 22 and a nipple 24 which is attached to the mouthpiece 22 so as to extend from one side thereof. The mouthpiece 22 includes a centrally-disposed body portion 26 and lip-engaging flange portions 28 which surround the body portions 26.

The mouthpiece 22 of the depicted apparatus 22 is a one-piece component which can, for example, be formed in a molding process so that the body portion 26 and the flange portions 28 are integrally joined together. However and as will be apparent herein, the mouthpiece of an apparatus embodying the principles of the present invention can be constructed as a multi-component item. Meanwhile, the nipple 24 is elongated in shape and has a bulbous end portion 48 which extends away from the mouthpiece 22 and which is adapted to be comfortably accepted by the mouth of an infant. Preferably, the nipple 24 is of a soft plastic construction, and the end portion, indicated 50 in FIG. 4, opposite the bulbous end portion 48 is securely joined to the mouthpiece 22. When the nipple 24 is accepted by the mouth of an infant, the flange portions 28 rest against the outer surfaces of the lips of the infant, as is the case with common styles of pacifiers. In this connection, the flange portions 28 are relatively broad and include smooth lip-engaging surfaces 25 which engage and span the lips of the lips of the infant when the nipple 24 is fully accepted by the mouth of the infant. To enhance the infant's comfort when the nipple 24 is accepted by the mouth of the infant, the lip-engaging surfaces 25 are somewhat C-shaped in form as the mouthpiece 22 is viewed from above in FIG. 2.

It is a feature of the apparatus 20 that it includes a pair of internal passageways 30, 32 which are adapted to conduct oxygen which is delivered to an inlet port 34 associated with the front of the mouthpiece 22 from a source 36 (FIG. 3) and out of a region of the mouthpiece 22 disposed adjacent the nostrils of an infant whose mouth accepts the nipple 24. More specifically, each of the internal passageways 30 or 32 includes an inlet 40 and an outlet 42, and each passageway inlet 40 is adapted to accept oxygen delivered thereto from the source 36 and each outlet 42 is disposed at a location along a surface 25 of the mouthpiece so that when the nipple 24 is accepted by the mouth of an infant, the outlet 42 is disposed adjacent (and in registry with) the nostrils of the infant so that the each outlet 42 is substantially in axial alignment with a corresponding nostril. In other words, within the depicted apparatus 20 and when the nipple 24 is accepted by the mouth of an infant, each outlet 42 is directed toward a corresponding nostril of the infant.

The inlet port 34, introduced earlier, is joined to the front of the body portion 26 of the mouthpiece 22 and is sized to be received by the end of an oxygen-conducting tube 44 (e.g. having an outer diameter of about one-fourth inch) inserted endwise thereover. The interior of the inlet port 34 opens to a common (cavity) region at which the inlets 40 are joined in flow communication. With the passageway inlets 40 in flow communication with the inlet port 34, oxygen which is delivered to the inlet port 34 by way of the tube 44 is permitted (by way of the internal passageways 30 or 32) to form two streams of oxygen which flow toward the infant's two nostrils.

It is also a feature of the apparatus 20 that the mouthpiece 22 includes a protuberance 46 formed adjacent the outlets 42 of the pair of passageways 30, 32 having surfaces 43 which act as a deflector for directing the streams of oxygen exiting the outlets 42 substantially toward the nostrils of the infant with which the apparatus 20 is used. Inasmuch as the passageway outlets 42 are spaced from the infant's nostrils and, as best shown in FIG. 3, are directed along a path which possesses an upwardly-directed component when the nipple 24 is fully accepted by the infant's mouth, the protuberance surfaces 43 are shaped to direct, or deflect, the oxygen flow stream which exits the outlets 42 so as to impart to the oxygen flow stream a larger horizontal component (with reference still to FIG. 3) so that the oxygen which exits the outlets 42 is directed substantially along a path which is directed toward the infant's nostrils. In other words, whereas the stream of oxygen which exits the outlets 42 of the depicted apparatus 20 is directed substantially upwardly with respect to the mouthpiece 22, the protuberance 46 serves to alter the path of the oxygen flow stream en route toward the infant's nostrils by imparting to the oxygen flow stream more of a horizontal path.

During use of the apparatus 20, the deflector-providing protuberance 46 helps to reduce the amount of oxygen which could otherwise be lost to the atmosphere, rather than being inhaled by a patient, and the protuberance 46 is advantageous in this respect. At the same time, neither the protuberance 46 nor any other portion of the apparatus 20 need be inserted into the nose of the infant for delivering most of the oxygen which exits the outlets 42 to the infant's nostrils, and the apparatus 20 is further advantageous in this respect.

It follows from the foregoing that an oxygen delivery apparatus 20 has been described for delivery of oxygen to an infant from an oxygen source 44 with no need that any tubes be inserted into the nostrils of the infant in order that oxygen be delivered effectively to an infant. The apparatus 20 includes a mouthpiece 22 having a central body portion 26 and lip-engaging flange portions 28 which surround the body portion 26 and further includes a nipple 24 which extends from the body portion 26 for acceptance by the mouth of an infant. In addition, the body portion 26 of the mouthpiece includes a pair of internal passageways 30, 32 each having an inlet 40 and an outlet 42. Furthermore, the inlets 40 of the passageways 30, 32 are adapted to accept oxygen delivered thereto from a source 36, and the outlets 42 of the passageways 30, 32 are disposed at locations along the surface of the mouthpiece 22 so that when the nipple 24 is accepted by the mouth of an infant, the outlets 42 of the passageways 30, 32 are disposed adjacent, but not within, the nostrils of the infant.

It will be understood that numerous modifications and substitutions can be had to the aforedescribed embodiment 20 without departing from the spirit of the invention. For example, although the aforedescribed embodiment 20 has been shown and described as including internal passageways 30, 32 which are formed within a single-component mouthpiece 22, the passageways 30, 32 can be formed between the surfaces of a multi-component mouthpiece. For example, there is illustrated in FIG. 5 an alternative apparatus 60 having a mouthpiece 62 including a front piece 64 which has a rear surface 66 and further includes a rear piece 68 which has a front surface 69. The rear surface 60 and the front surface 69 are adapted to abut one another when the front and rear pieces 64 and 68 are joined together into a single mouthpiece 62. Within this embodiment 60, a pair of grooves 70, 72, joined at an apex 74, are formed within the front surface 69 of the rear piece 68 so that the (upper ends of the) grooves 70, 72 open out of the rear piece 68 along the upper edge 78 thereof.

When the front and rear pieces 64 and 68 are joined together so that the surfaces 66 and 69 are in abutting relationship with one another, the grooves 70, 72 provide the pair of internal passageways through which oxygen is conducted to the rear piece 68 and out of the upper edge 78 thereof. The front piece 66 includes an inlet 76 which is in flow communication with the apex 74 of the grooves 70, 72 so that when an oxygen-conducting tube is positioned about the inlet port 76, oxygen from a source (e.g. the FIG. 3 source 36) is conducted out of the mouthpiece 62 through the passageway outlets disposed adjacent the upper edge 78 of the rear piece 68. In addition to the inlet port 76, the front piece 64 also includes a deflector-providing protuberance 80 along the upper edge 78 thereof so that when the front and rear pieces 64 and 68 are secured together to form the single mouthpiece 62, the protuberance 80 acts to deflect the oxygen which exits these grooves 70, 72, or passageways, substantially toward the nostrils of an infant who uses the apparatus 60.

Figure 6:
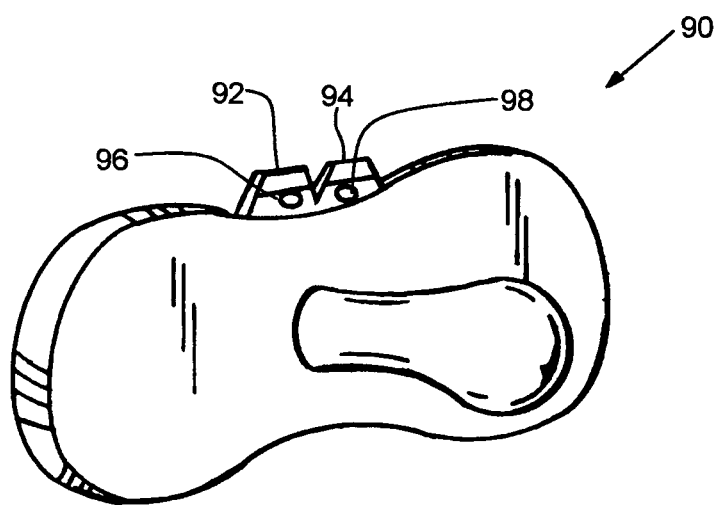
FIG. 6 is a perspective view of one more oxygen-delivery apparatus within which features of the present invention are embodied.

Furthermore and although the aforedescribed apparatus 20 has been shown and described as including a single deflector-providing protuberance 46, an apparatus embodying features of the present invention can embody an alternative number of deflector-providing protuberances. For example, there is illustrated in FIG. 6 an oxygen-delivery apparatus 90 having a pair of deflector-providing protuberances 92, 94 wherein each of protuberance 92 or 94 possesses deflector surfaces which are disposed adjacent a corresponding outlet, indicated 96 or 98, of the internal passageways of the apparatus 90 for altering the flow stream of oxygen which exits a corresponding outlet, indicated 96 or 98, of the internal passageways of the apparatus 90 so that the oxygen flow stream continues to move along a path which is directed toward a nostril of the infant.

Accordingly, the aforedescribed embodiment 20 is intended for the purpose of illustration and not as limitation.

The invention claimed is:

1. An oxygen delivery apparatus for delivery of oxygen from an oxygen source to an infant having nostrils and a mouth including lips, the apparatus comprising:
a mouthpiece having a body portion and lip-engaging flange portion which surround the body portion; and
a nipple which extends from the body portion for acceptance by the mouth of the infant; and
wherein the body portion of the mouthpiece forms a bifurcated air passage comprising a pair of continuous internal passageways each having an inlet and an outlet and wherein the inlets of the passageways are adapted to accept oxygen delivered thereto from the oxygen source and delivered to the inlets of the internal passageways by a single inlet port and wherein the outlets of the passageways are disposed at locations along the surface of the mouthpiece so that when the nipple is accepted by the mouth of the infant, the outlets of the passageways are disposed adjacent, but not within, the nostrils of the infant; and
wherein the mouthpiece includes two upright protuberances situated adjacent the outlets of the passageways, each protuberance having a deflector surface for directing the flow of oxygen exiting the outlets of the passageways along a path which is directed substantially toward the nostrils of the infant.

2. The apparatus as defined in claim 1 wherein the lip-engaging flange portion has a lip-engaging surface which engages and spans the lips of the infant when the nipple is fully accepted by the mouth of the infant, and the outlets of the passageways open out of the lip-engaging surface of the flange portion at locations adjacent the nostrils of the infant.

3. The apparatus as defined in claim 1 wherein the inlets of the passageways are in flow communication with one another for accepting oxygen delivered thereto from the oxygen source.

4. The apparatus as defined in claim 3 wherein the mouthpiece includes an inlet port to which an oxygen conducting tube can be connected for delivering oxygen from the oxygen source to the passageways of the mouthpiece.

5. The apparatus as defined in claim 4 wherein the inlet port is disposed on a side of the body portion of the mouthpiece opposite the nipple.

6. The apparatus as defined in claim 1 wherein the body portion of the mouthpiece is constructed of multiple pieces having surfaces which abut one another when the pieces are joined together to form the body of the mouthpiece, and the passageways are provided by grooves defined between the abutting surfaces of the multiple pieces.

7. The apparatus as defined in claim 1 wherein the mouthpiece and nipple provide a pacifier for the infant.

8. An oxygen delivery apparatus for delivery of oxygen from an oxygen source to an infant having nostrils and a mouth including lips, the apparatus comprising:
a mouthpiece having a body portion and lip-engaging flange portion which surround the body portion; and
a nipple which extends from the body portion for acceptance by the mouth of the infant and wherein the lip-engaging flange portion has a lip-engaging surface which engages and spans the lips of the infant when the nipple is fully accepted by the mouth of the infant; and
wherein the body portion of the mouthpiece forms a bifurcated air passage comprising a pair of continuous internal passageways each having an inlet and an outlet and wherein the inlets of the passageways are adapted to accept oxygen delivered thereto from the oxygen source and delivered to the inlets of the internal passageways by a single inlet port and wherein the outlets of the passageways are disposed at locations along the lip-engaging surface of the lip-engaging flange portion so that when the nipple is fully accepted by the mouth of the infant, the outlets of the passageways are disposed adjacent, but not within, the nostrils of the infant; and
wherein the mouthpiece includes two upright protuberances situated adjacent the outlets of the passageways, each protuberance having a deflector surface for directing the flow of oxygen exiting the outlets of the passageways along a path which is directed substantially toward the nostrils of the infant.

9. The apparatus as defined in claim 8 wherein the inlets of the passageways are in flow communication with one another for accepting oxygen delivered thereto from the oxygen source.

10. The apparatus as defined in claim 9 wherein the mouthpiece includes an inlet port to which an oxygen conducting tube can be connected for delivering oxygen from the oxygen source to the passageways of the mouthpiece.

11. The apparatus as defined in claim 10 wherein the inlet port is disposed on a side of the body portion of the mouthpiece opposite the nipple.

12. The apparatus as defined in claim 8 wherein the body portion of the mouthpiece is constructed of multiple pieces having surfaces which abut one another when the pieces are joined together to form the body of the mouthpiece, and the passageways are provided by grooves defined between the abutting surfaces of the multiple pieces.

13. The apparatus as defined in claim 8 wherein the mouthpiece and nipple provide a pacifier for the infant.

14. An oxygen delivery apparatus for delivery of oxygen from an oxygen source to an infant having nostrils and a mouth including lips, the apparatus comprising:
a mouthpiece having a unitary body portion having a lip-engaging flange portion which surrounds the body portion, and an integrated bifurcated air passage comprising a pair of continuous internal passageways within the body portion; and
a nipple which extends from the body portion for acceptance by the mouth of the infant; and
wherein the internal air passageways formed within the mouthpiece comprise a single air inlet port disposed on a first surface of the mouthpiece and adapted to accept oxygen delivered thereto, the air passageway being bifurcated within the mouthpiece to form two discreet nasal cannulae, each nasal cannula having an outlet port disposed along a second surface of the mouthpiece so that when the nipple is accepted by the mouth of the infant, the outlet ports are disposed in axial alignment with and adjacent to, but not within, the nostrils of the infant; and
wherein the mouthpiece includes two upright protuberances situated adjacent the outlets of the passageways, each protuberance having a deflector surface for directing the flow of oxygen exiting the outlets of the passageways along a path which is directed substantially toward the nostrils of the infant.

15. The apparatus of claim 14 wherein the two upright protuberances are hood-shaped.

16. The apparatus of claim 14 wherein apparatus further comprises an upper edge and a lower edge and wherein the single air inlet port is disposed on the first surface of the mouthpiece between the lower edge and the nipple.

17. The apparatus of claim 14 wherein the lip-engaging flange portion has a lip-engaging surface which engages and spans the lips of the infant when the nipple is fully accepted by the mouth of the infant, and the outlets of the passageway open out of the lip-engaging surface of the flange portion at locations adjacent the nostrils of the infant.

* * * * *